(12) United States Patent
Siochi (10) Patent No.: US 6,661,871 B2
(45) Date of Patent: Dec. 9, 2003

(54) SYSTEM AND METHOD FOR OPTIMIZING RADIATION TREATMENT WITH AN INTENSITY MODULATING MULTI-LEAF COLLIMATOR BY MINIMIZING JUNCTIONS

(75) Inventor: Ramon Alfredo Carvalho Siochi, Apex, NC (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 243 days.

(21) Appl. No.: 09/967,673

(22) Filed: Sep. 28, 2001

(65) Prior Publication Data

US 2003/0072410 A1 Apr. 17, 2003

(51) Int. Cl.[7] ................................................ A61N 5/10
(52) U.S. Cl. ......................................... 378/65; 378/150
(58) Field of Search ........................... 378/65, 147–152

(56) References Cited

U.S. PATENT DOCUMENTS

| | | | |
|---|---|---|---|
| 5,663,999 A | 9/1997 | Siochi | 378/65 |
| 5,724,403 A | 3/1998 | Siochi et al. | 378/150 |
| 6,314,159 B1 * | 11/2001 | Siochi | 378/65 |
| 6,330,300 B1 * | 12/2001 | Siochi | 378/65 |
| 6,349,129 B1 * | 2/2002 | Siochi | 378/65 |

* cited by examiner

Primary Examiner—David V. Bruce
Assistant Examiner—Jurie Yun (57) ABSTRACT

A system and method of the present invention for controlling radiation delivery from a radiation source to an object are disclosed. The method generally includes defining a field on the object for radiation delivery. The field includes a plurality of cells, each having a defined treatment intensity level. The cells are grouped to form a matrix having at least one dimension approximately equal to a width of a collimator leaf capable of blocking radiation emitted from the radiation source. The method further includes decomposing the matrix into orthogonal matrices and optimizing delivery of the radiation by selecting a combination of orthogonal matrices to minimize junction effects.

29 Claims, 12 Drawing Sheets

$^{90}m1,1=$ $\begin{array}{|c|c|}\hline 0 & 0 \\\hline 2 & 2 \\\hline\end{array}$ $^{90}m1,3=$ $\begin{array}{|c|c|}\hline 0 & 0 \\\hline 2 & 2 \\\hline\end{array}$ $^{0}m1,1=$ $\begin{array}{|c|c|}\hline 0 & 1 \\\hline 0 & 1 \\\hline\end{array}$ $^{0}m1,3=$ $\begin{array}{|c|c|}\hline 0 & 1 \\\hline 0 & 1 \\\hline\end{array}$

FIG. 12

$^{90}u1,1=$ $\begin{array}{|c|c|}\hline 0 & 0 \\\hline 0 & 0 \\\hline\end{array}$ $^{90}u1,3=$ $\begin{array}{|c|c|}\hline 0 & 0 \\\hline 0 & 0 \\\hline\end{array}$ $^{0}u1,1=$ $\begin{array}{|c|c|}\hline 1 & 1 \\\hline 1 & 1 \\\hline\end{array}$ $^{0}u1,3=$ $\begin{array}{|c|c|}\hline 3 & 3 \\\hline 3 & 3 \\\hline\end{array}$

FIG. 13a $^{90}u1,1=$ $\begin{array}{|c|c|}\hline 0 & 0 \\\hline 0 & 0 \\\hline\end{array}$ $^{90}u1,3=$ $\begin{array}{|c|c|}\hline 1 & 1 \\\hline 1 & 1 \\\hline\end{array}$ $^{0}u1,1=$ $\begin{array}{|c|c|}\hline 1 & 1 \\\hline 1 & 1 \\\hline\end{array}$ $^{0}u1,3=$ $\begin{array}{|c|c|}\hline 2 & 2 \\\hline 2 & 2 \\\hline\end{array}$

FIG. 13b $^{90}u1,1=$ $\begin{array}{|c|c|}\hline 0 & 0 \\\hline 0 & 0 \\\hline\end{array}$ $^{90}u1,3=$ $\begin{array}{|c|c|}\hline 2 & 2 \\\hline 2 & 2 \\\hline\end{array}$ $^{0}u1,1=$ $\begin{array}{|c|c|}\hline 1 & 1 \\\hline 1 & 1 \\\hline\end{array}$ $^{0}u1,3=$ $\begin{array}{|c|c|}\hline 1 & 1 \\\hline 1 & 1 \\\hline\end{array}$

SYSTEM AND METHOD FOR OPTIMIZING RADIATION TREATMENT WITH AN INTENSITY MODULATING MULTI-LEAF COLLIMATOR BY MINIMIZING JUNCTIONS

FIELD OF THE INVENTION

The present invention relates generally to a radiation emitting device, and more particularly, to a system and method for efficiently delivering radiation treatment.

BACKGROUND OF THE INVENTION

Radiation emitting devices are generally known and used, for instance, as radiation therapy devices for the treatment of patients. A radiation therapy device generally includes a gantry which can be swiveled around a horizontal axis of rotation in the course of a therapeutic treatment. A linear accelerator is located within the gantry for generating a high energy radiation beam for therapy. This high energy radiation beam may be an electron beam or photon (x-ray) beam, for example. During treatment, the radiation beam is trained on a zone of a patient lying in the isocenter of the gantry rotation.

In order to control the radiation emitted toward the patient, a beam shielding device, such as a plate arrangement or collimator, is typically provided in the trajectory of the radiation beam between the radiation source and the patient. An example of a plate arrangement is a set of four plates which can be used to define an opening for the radiation beam. The collimator is a beam shielding device which may include multiple leaves (e.g., relatively thin plates or rods) typically arranged as opposing leaf pairs. The plates are formed of a relatively dense and radiation impervious material and are generally independently positionable to delimit the radiation beam.

The beam shielding device defines a field on the zone of the patient for which a prescribed amount of radiation is to be delivered. The usual treatment field shape results in a three-dimensional treatment volume which includes segments of normal tissue, thereby limiting the dose that can be given to the tumor. The dose delivered to the tumor can be increased if the amount of normal tissue being irradiated is decreased and the dose delivered to the normal tissue is decreased. Avoidance of delivery of radiation to the healthy organs surrounding and overlying the tumor limits the dosage that can be delivered to the tumor.

The delivery of radiation by a radiation therapy device is typically prescribed by an oncologist. The prescription is a definition of a particular volume and level of radiation permitted to be delivered to that volume. Actual operation of the radiation equipment, however, is normally done by a therapist. The radiation emitting device is programmed to deliver the specific treatment prescribed by the oncologist. When programming the device for treatment, the therapist has to take into account the actual radiation output and has to adjust the dose delivery based on the plate arrangement opening to achieve the prescribed radiation treatment at the desired depth in the target.

The radiation therapist's challenge is to determine the best number of fields and intensity levels to optimize dose volume histograms, which define a cumulative level of radiation that is to be delivered to a specified volume. Typical optimization engines optimize the dose volume histograms by considering the oncologist's prescription, or three-dimensional specification of the dosage to be delivered. In such optimization engines, the three-dimensional volume is broken into cells, each cell defining a particular level of radiation to be administered. The outputs of the optimization engines are intensity maps, which are determined by varying the intensity at each cell in the map. The intensity maps specify a number of fields defining optimized intensity levels at each cell. The fields may be statically or dynamically modulated, such that a different accumulated dosage is received at different points in the field. Once radiation has been delivered according to the intensity map, the accumulated dosage at each cell, or dose volume histogram, should correspond to the prescription as closely as possible.

In such intensity modulation, junctions can appear between the boundary of a field defined by the tip of a leaf that is common to a boundary of a second non-intersecting field formed by the side of a leaf in a collimator setting orthogonal to that of the first field. This may result in underdosage effects and reduce resolution at some locations in an intensity map.

Accordingly, there is therefore, a need for a system and method for achieving higher spatial resolution intensity modulation radiation therapy by removing the underdosage effects that can occur at junctions between orthogonal fields.

SUMMARY OF THE INVENTION

A method and system for controlling radiation delivery from a radiation source to an object are disclosed.

A method of the present invention generally comprises defining a field on the object for radiation delivery. The field includes a plurality of cells, each having a defined treatment intensity level. The cells are grouped to form a matrix having at least one dimension approximately equal to a width of a collimator leaf capable of blocking radiation emitted from the radiation source. The method further includes decomposing the matrix into orthogonal matrices and optimizing delivery of the radiation by selecting a combination of orthogonal matrices to minimize junction effects.

A system of the present invention generally comprises a collimator having multiple leaves for blocking radiation from the source and defining an opening between the radiation source and object. The system further includes a processor for receiving a matrix comprising a plurality of cells having at least one dimension approximately equal to a width of one of the collimator leaves, decomposing the matrix into orthogonal matrices, and optimizing delivery of the radiation output by selecting a combination of orthogonal matrices to minimize junction effects.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

FIGS. 13a–13h illustrate different possible zero degree offset and ninety degree offset uniform matrices based on the uniform matrices of FIG. 10.

Corresponding reference characters indicate corresponding parts throughout the several views of the drawings.

DETAILED DESCRIPTION OF THE PREFERRED EMBODIMENTS

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to the embodiments shown, but is to be accorded the widest scope consistent with the principles and features described herein. For purpose of clarity, details relating to technical material that is known in the technical fields related to the invention have not been described in detail.

Figure 1:
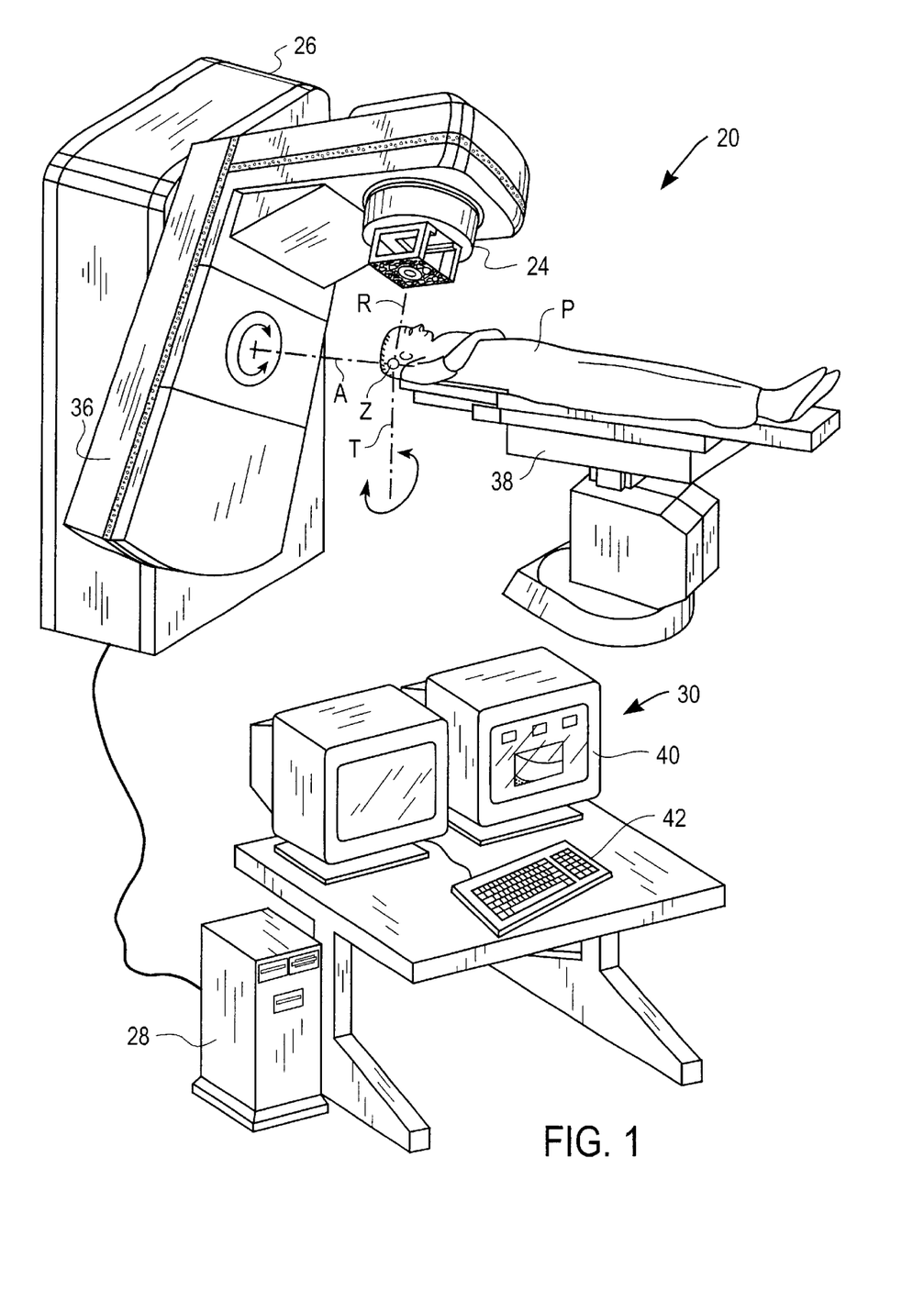
FIG. 1 is a diagram of a radiation treatment device and treatment console according to an embodiment of the present invention and a patient positioned for treatment within the treatment device.

Referring now to the drawings, and first to FIG. 1, a radiation treatment device of the present invention is shown and generally indicated at 20. The radiation treatment device 20 includes a beam shielding device (not shown) within a treatment head 24, a control unit within a housing 26 connected to a treatment processing unit, generally indicated at 30. The radiation treatment device further includes a gantry 36 which can be swiveled for rotation about axis A in the course of a therapeutic treatment. The treatment head 24 is fixed to the gantry 36 for movement therewith and a linear accelerator is located within the gantry for generating high powered radiation used for therapy. The radiation emitted from the linear accelerator extends generally along axis R. Electron, photon, or any other detectable radiation may be used for the therapy. During treatment, the radiation beam is focused on a zone Z of an object P (e.g., a patient who is to be treated). The zone to be treated is located at an isocenter defined by the intersection of the rotational axis A of the gantry 36, rotational axis T of treatment table 38, and the radiation beam axis R. The rotatable gantry 36 allows for different beam angles and radiation distributions without having to move the patient.

The treatment processing unit 30 is used to input information, such as radiation intensity and location of treatment, into the radiation treatment device 20 and output data for monitoring of the treatment. The processing unit 30 includes an output device such as a visual display monitor 40 and an input device such as a keyboard 42. The treatment processing unit 30 is typically operated by a therapist who administers actual delivery of radiation treatment as prescribed by an oncologist. The therapist uses the keyboard 42 to enter data, which defines the radiation dose to be delivered to the patient, into the processing unit 30. The data may also be input via other input devices, such as a data storage device, for example. Various types of data can be displayed before and during the treatment on the screen of the display monitor 40.

Figure 2:
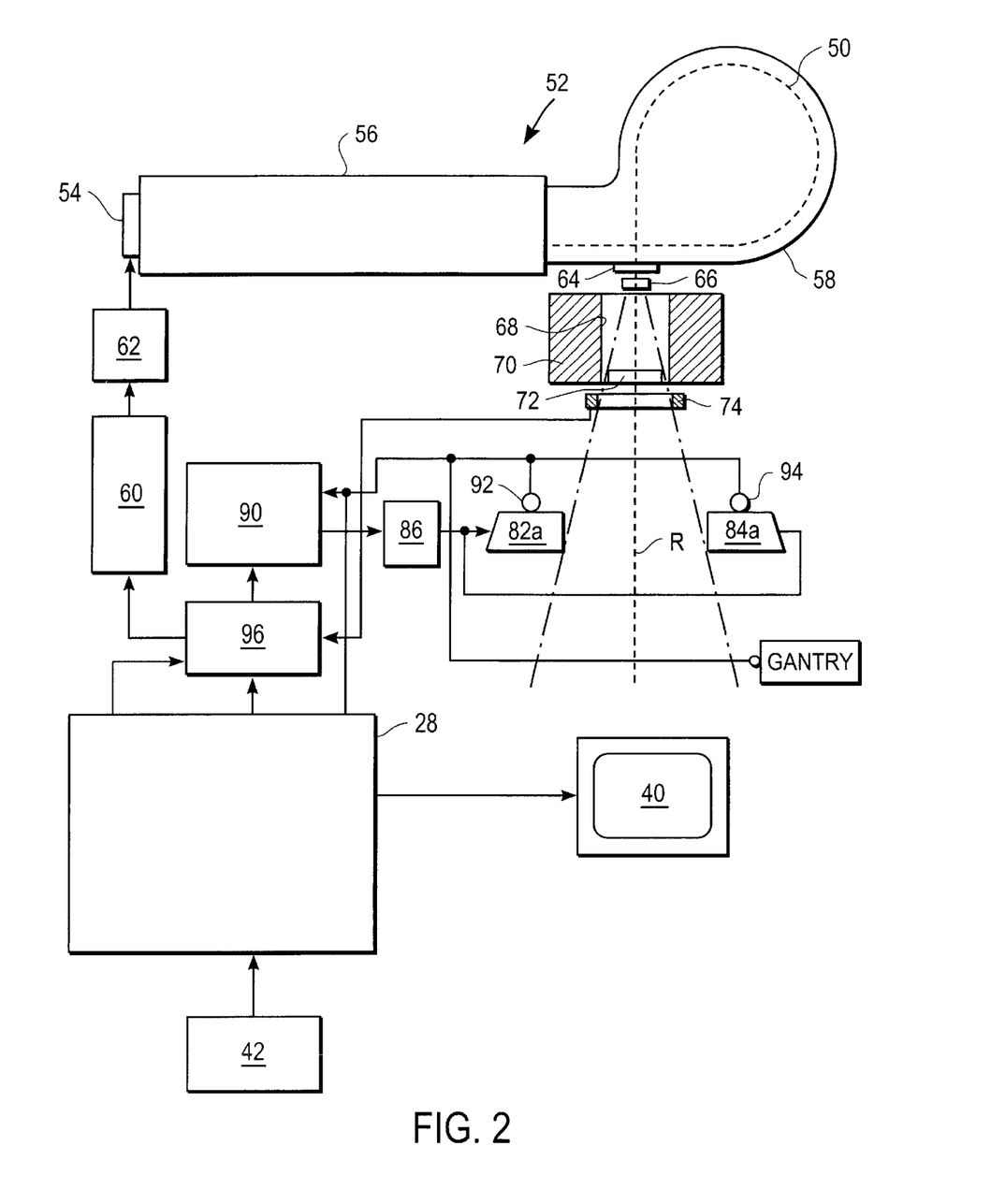
FIG. 2 is a block diagram illustrating portions of the radiation treatment device of FIG. 1.

FIG. 2 is a block diagram of the radiation treatment device 20 showing portions of the treatment processing unit 30 in further detail. An electron beam 50 is generated in an electron accelerator, generally indicated at 52. The electron accelerator 52 includes an electron gun 54, wave guide 56, and an evacuated envelope or guide magnet 58. A trigger system 60 generates injector trigger signals and supplies them to an injector 62. Based on these injector trigger signals, the injector 62 generates injector pulses which are fed to the electron gun 54 in the accelerator 52 for generating electron beam 50. The electron beam 50 is accelerated and guided by the wave guide 56. For this purpose, a high frequency source (not shown) is provided, which supplies radio frequency signals for the generation of an electromagnetic field supplied to the wave guide 56. The electrons injected by the injector 62 and emitted by the electron gun 54 are accelerated by the electromagnetic field in the wave guide 56 and exit at the end opposite the electron gun 54 to form electron beam 50. The electron beam 50 then enters the guide magnet 58 and from there is guided through a window 64 along axis R. After passing through a scattering foil 66 for electron mode (or target for photon mode), the beam 50 passes through a passageway 68 of a shield block 70 and encounters a secondary scattering foil 72 for electron mode (or flattening filter for photon mode). The beam next passes through a measuring chamber 74 in which the dose is ascertained.

Figure 3:
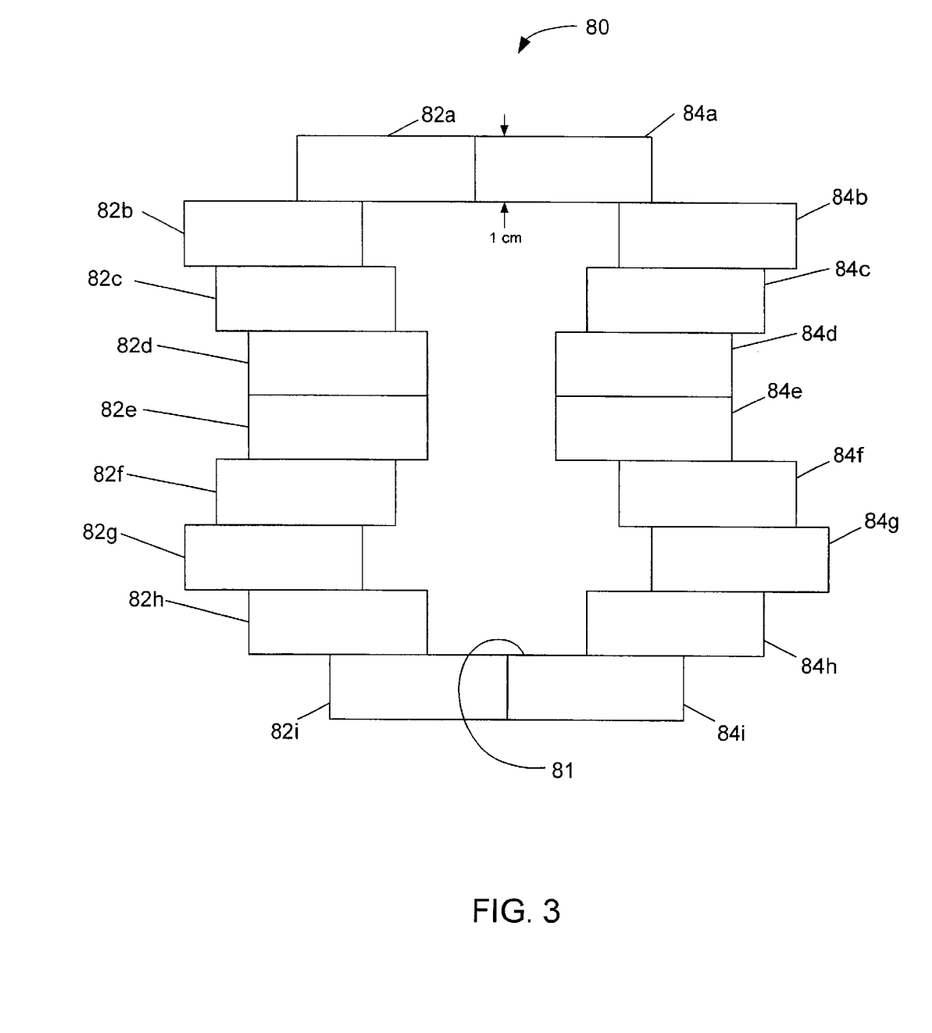
FIG. 3 is a schematic illustrating leaves of a multi-leaf collimator positioned for treatment in the radiation treatment device of FIG. 1.

A beam shielding device, generally indicated at 80, is provided in the path of the beam 50 to define a radiation field 81 (FIGS. 2 and 3). The beam shielding device 80 includes a plurality of opposing plates or leaves 82a–i and 84a–i, only two of which are shown in FIG. 2 for simplification. FIG. 3 illustrates leaves 82a–i and 84a–i (forming leaf pairs 82a and 84a, 82b and 84b, . . . , 82i and 84i) of a multi-leaf collimator mounted between the radiation source and patient and positioned to define a treatment field by delimiting the electron beam 50. The leaves 82a–i, 84a–i typically have a one centimeter width and are substantially impervious to the emitted radiation so that they block healthy tissue from the radiation.

The leaves 82a–i, 84a–i are movable in a direction generally perpendicular to axis R by a drive unit 86 (which is shown in FIG. 2 only with respect to plate 82a) to change the size of the irradiated field so that the distribution of radiation over the field does not need to be uniform (i.e., one region may be exposed to a higher dose than another region). The drive unit 86 includes an electric motor which is coupled to the plate 82a and controlled by a motor controller 90. Position sensors 92, 94 are also coupled to plates 82a, 84a, respectively, for sensing their positions. The drive unit 86 drives the plate 82a in and out of the treatment field, thus creating the desired field shapes.

The motor controller 90 is coupled to a dose control unit 96 which includes a dosimetry controller coupled to the central processing unit 28 for providing set values for the radiation beam for achieving given isodose curves (FIG. 2). The output of the radiation beam is measured by the measuring chamber 74. In response to the deviation between the set values and the actual values, the dose control unit 96 supplies signals to the trigger system 60 which change in a known manner the pulse repetition frequency so that the deviation between the set values and the actual values of the radiation beam output is minimized. The dose absorbed by the patient is dependent upon movement of the collimator plates 82a, 84a. The central processing unit 28 controls execution of the program and the opening and closing of the collimator plates 82a, 84a to deliver radiation according to a desired intensity profile. The central processing unit 28 may include other features described in U.S. Pat. No. 5,724,403, which is incorporated herein by reference in its entirety, for example.

It is to be understood that the radiation treatment device may be different than the one described and shown herein without departing from the scope of the invention. The treatment device 20 described above is provided as an example of a device for use in delivering a treatment developed by the optimization process described below.

The following describes a method for optimizing radiation treatment. A method for optimizing treatment by reducing the number of segments required to deliver the modulated radiation therapy is first described followed by a description of how to simultaneously minimize the number of potential junction effects and the number of segments. The reduction in segments results in shorter delivery times while minimizing the junctions results in a reduction in underdosage effects. As described below, the minimization is generally achieved by reducing high leaf direction gradients in component intensity maps.

Figure 4:
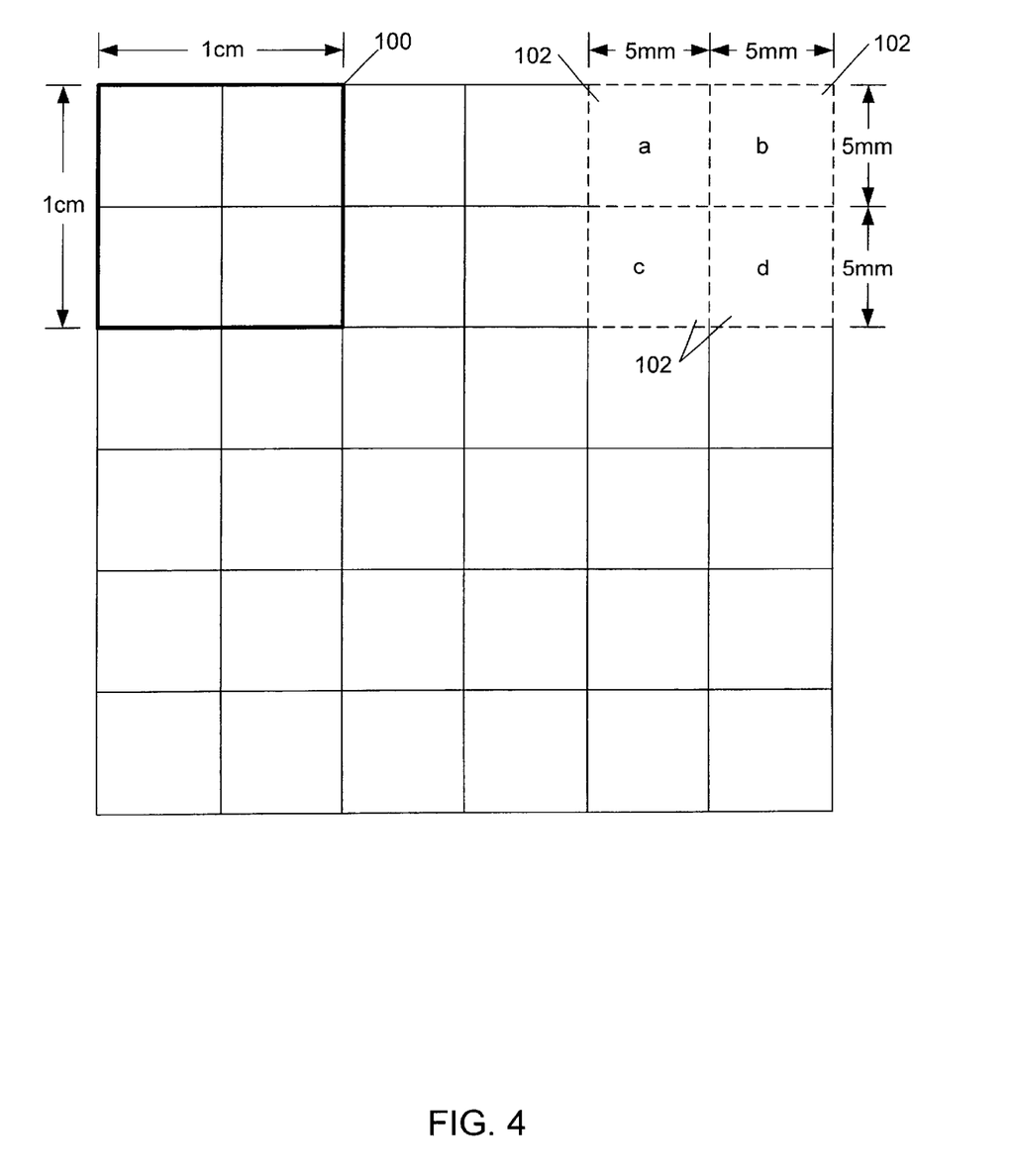
FIG. 4 is a schematic illustrating cells located in an intensity map.

FIG. 4 illustrates an intensity map having a plurality of 1 cm×1 cm macrocells 100 (indicated by dark lines) divided into four 5 mm×5 mm microcells 102 (indicated by dashed lines). The 5 mm×5 mm microcells 102 are used to convert macrocell 100 into two orthogonal intensity maps (component maps), one with a resolution of 5 mm×10 mm, and the other with a resolution of 10 mm×5 mm. An example of a process for dividing the intensity map into groups of four 5 mm×5 mm microcells 102 is described in U.S. patent application Ser. No. 09/234,364, by Siochi, filed Jan. 20, 1999, which is incorporated herein by reference in its entirety. This grouping of 5 mm×5 mm microcells 102 allows for treatment of a field with a 5 mm×5 mm resolution using a multi-leaf collimator having one centimeter leaves, as shown in FIG. 3.

Figure 5:
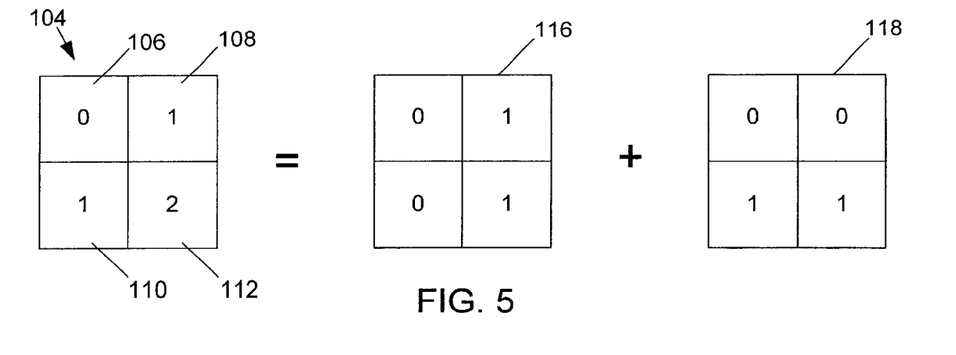
FIG. 5 is a diagram of a matrix broken down into a zero degree matrix component and a ninety degree matrix component.
Figure 6:
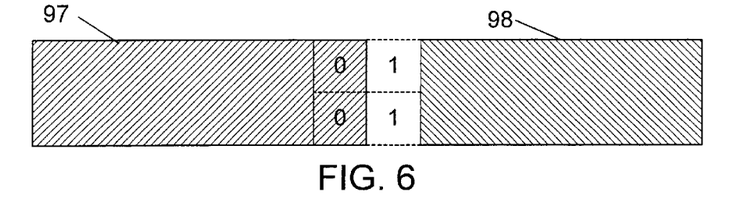
FIG. 6 is a plan view of an opposing pair of leaves configured to apply a dosage specified by the zero degree matrix of FIG. 5.
Figure 7:
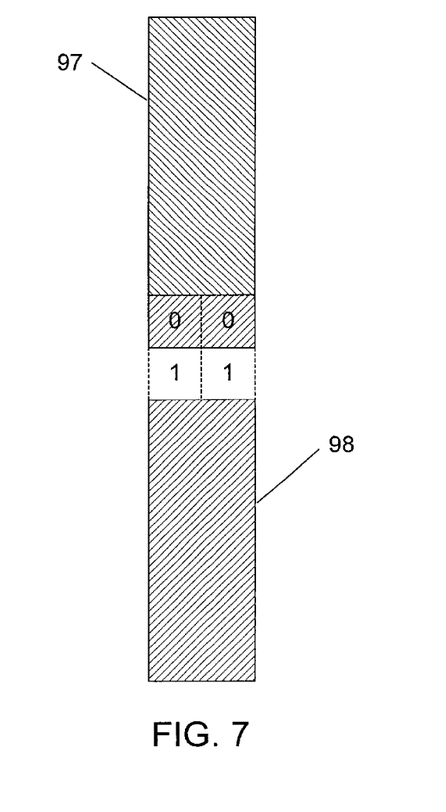
FIG. 7 is a plan view of an opposing pair of leaves configured to apply a dosage specified by the ninety degree matrix of FIG. 5.

FIG. 5 illustrates an example of a matrix, generally indicated at 104 formed from an intensity map composed of four 5 mm×5 mm microcells 106, 108, 110, 112. Each microcell 106, 108, 110, 112 identifies a section in a field to be treated with radiation. The numbers (0, 1, 1, 2) within each microcell 106, 108, 110, 112, respectively, represent the radiation intensity level for locations within the field and are in monitor units (mu) or relative monitor unit intensities (e.g., $1 \times 10^2$ mu). In order to provide 5 mm×5 mm resolution for the intensity map, the matrix 104 is broken down into two orthogonal matrices, 116, 118 having a 1 cm×5 mm resolution and 5 mm×1 cm resolution, respectively. A one centimeter leaf width multi-leaf collimator may then be used to deliver the intensity map with a 5 mm×5 mm resolution. For example, a pair of leaves 97, 98 positioned as shown in FIG. 6 may be used to deliver the map intensity shown in matrix 116 of FIG. 5. A dose of radiation (e.g., 1 mu) is applied to fields corresponding to microcells 108 and 112 of matrix 104. The collimator is then rotated approximately ninety degrees to deliver the map intensity shown in matrix 118 with the leaf position shown in FIG. 7. With the collimator rotated ninety degrees, a dose of radiation (e.g., 1 mu) is applied to the fields corresponding to microcells 110 and 112 of matrix 104. The two radiation applications result in a 2 mu dose to the field corresponding to microcell 112, a 1 mu dose to the fields corresponding to microcells 108 and 110, and no radiation being applied to the field corresponding to microcell 106. The decomposition of the matrix 104 into orthogonal matrices 116 and 118 thus provides for 5 mm×5 mm resolution treatment using collimator leaves having a one centimeter width.

In the following description, the original input intensity map is defined as a macromatrix and the groups of four microcells within the macromatrix are defined as micromatrices (or matrices). In order for the intensity map to be decomposed into orthogonal maps, the vertical gradients of each column of the micromatrix (matrix) 100 must be equal to one another and the horizontal gradients of each row of the micromatrix must also be equal to one another (FIG. 4). This provides a 1 cm×1 cm area under the intersection of one leaf pair for one collimator setting and another leaf pair for the orthogonal collimator setting. For example, if the horizontal gradients are equal for the micromatrix having cells 102 (shown in FIG. 4) the following equation must apply:

$$b-a=d-c;$$

where: a, b, c, d are the intensity values corresponding to locations in the micromatrix 102 of FIG. 4

Similarly, if the vertical gradients are equal the following equation must apply:

$$c-a=d-b.$$

The following describes a method for defining two orthogonal maps, a zero degree map for application with a zero degree offset collimator setting, and a ninety degree map for application with an orthogonal collimator setting. Several decompositions of an intensity map are possible to create the two orthogonal maps. The optimization method described below may be used to find the decompositions which yield the shortest delivery time to minimize overall treatment time and increase the life of the radiation treatment device. Preferably, orthogonal maps having the lowest sum of horizontal gradients (for zero offset maps only) and vertical gradients (for ninety degree offset maps only) are selected through an optimization process to provide matrices resulting in an efficient method of treatment. The following example uses an intensity map represented by a two by four matrix (FIG. 8), however, the intensity map may have a size different than shown herein and may be mapped using various size matrices. Also, the intensity map may be broken down into microcells having a dimension other than 5 mm×5 mm if a different resolution is required. For example, each macrocell may be divided into nine microcells in which case the intensity map may be deliverable as two orthogonal intensity maps having a resolution of 1 cm×⅓ cm and ⅓ cm×1 cm (see, for example, U.S. patent application Ser. No. 09/234,364, referenced above). Also, a multi-leaf collimator having leaves with a width other than 1 cm may be used, and the size of the corresponding microcells will be 1/n times the leaf width (where n is a positive integer (e.g., 2 or 3).

Figure 8:
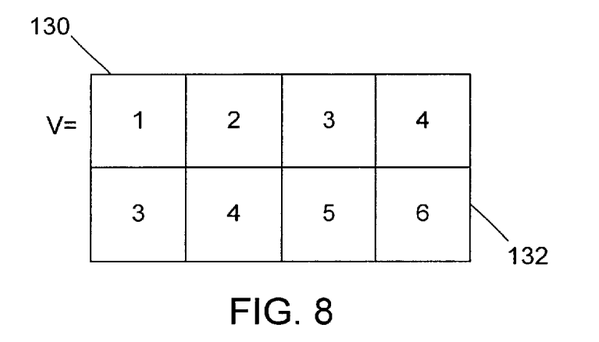
FIG. 8 is a diagram of a macromatrix used to illustrate an example of an optimization process of the present invention.

FIG. 8 shows a macromatrix V having eight cells, each identified by the row (i) and column (j) that the cell is located in. For example, the upper left hand cell 130 is identified as V1,1 (i=1, j=1) and the lower right hand cell 132 is identified as V2,4 (i=2, j=4). The macromatrix V may be broken down into a uniform matrix U and a microgradient matrix M. The microgradient matrix M is formed by subtracting out from each group of all four cells (micromatrix) the minimum value among them. Thus, the microgradient matrix M will have at least one zero in each group of four cells (micromatrix). The minimum value is then used to create the uniform matrix U, with the following relationship between the original matrix V, uniform matrix U and microgradient matrix M:

$$V = U + M.$$

Figure 9:
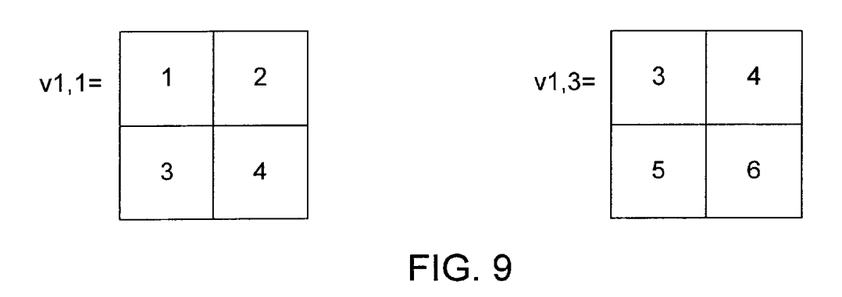
FIG. 9 is a diagram of two micromatrices of the macromatrix of FIG. 8.
Figure 10:
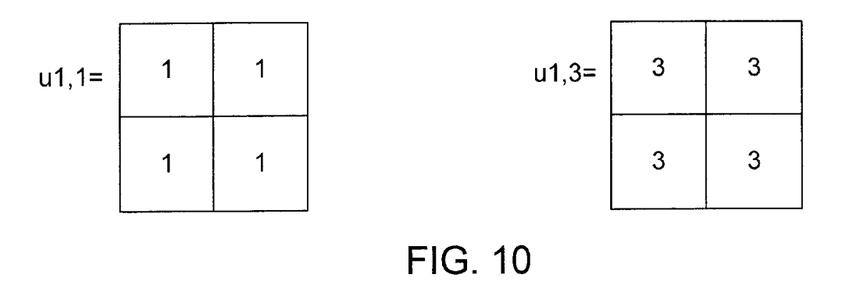
FIG. 10 is a diagram of uniform matrices formed from the micromatrices of FIG. 9 for use in the optimization process.
Figure 11:
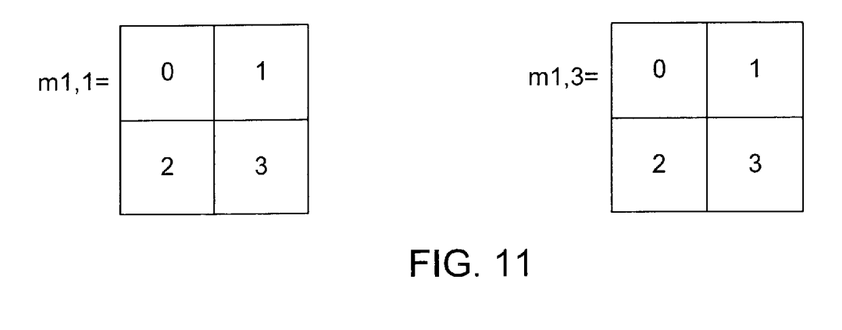
FIG. 11 is a diagram of microgradient matrices formed from the micromatrices of FIG. 9 for use in the optimization process.

The macromatrix V is first broken into micromatrices v1,1 and v1,3, each composed of four microcells (FIG. 9). In the following description, the micromatrices v1,1 and v1,3 are identified by the cell located in the upper left hand corner of the macromatrix V (i.e., cells 1,1 and 1,3) and the individual cells within the micromatrices are identified by their original cell location (i,j) in the macromatrix V. The micromatrices v1,1 and v1,3 may then be broken up into uniform matrices u1,1, u1,3 (FIG. 10) and microgradient matrices m1,1, m1,3 (FIG. 11). The uniform matrices are made up of cells having the minimum intensity value of its micromatrix v (i.e., 1 for matrix v1,1 and 3 for matrix v1,3). The uniform matrices u1,1 and u1,3 may therefore, be defined as follows:

$$u1,1 = \text{Min}(v(2,2), v(2,1), v(1,2), v(1,1));$$

and $$u1,3 = \text{Min}(v(2,4), v(2,3), v(1,4), v(1,3)).$$

All elements within the uniform matrix $u_{i,j}$ are equal to the minimum value of its micromatrix $v_{i,j}$:

$$u(2,2) = u(2,1) = u(1,2) = u(1,1);$$

and $$u(2,4) = u(2,3) = u(1,4) = u(1,3)$$

The microcells for the microgradient matrix $m_{i,j}$ are calculated as the difference between the respective micromatrix $v_{i,j}$ cells and uniform matrix $u_{i,j}$ cells as follows:

$$m1,1(i,j) = v1,1(i,j) - u1,1(i,j);$$

and $$m1,3(i,j) = v1,3(i,j) - u1,3(i,j).$$

The uniform matrices u1,1, u1,3 and microgradient matrices m1,1, m1,3 are each decomposed into two orthogonal subfields, a zero offset field $^0u_{i,j}$, $^0m_{i,j}$ (for application with the same collimator orientation as the original input matrix) and a ninety degree offset field $^{90}u_{i,j}$, $^{90}m_{i,j}$ (for application with the collimator rotated ninety degrees relative to the original input matrix's collimator orientation). The zero offset field and ninety degree offset fields may be defined as follows:

$$m_{i,j} = {^0m_{i,j}} + {^{90}m_{i,j}};$$

and $$u_{i,j} = {^0u_{i,j}} + {^{90}u_{i,j}}.$$

Figure 12:
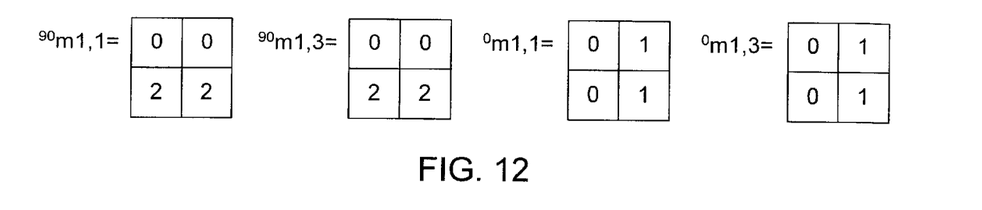
FIG. 12 illustrates the microgradient matrices of FIG. 11 broken into zero degree offset and ninety degree offset matrices.
Figure 13A:
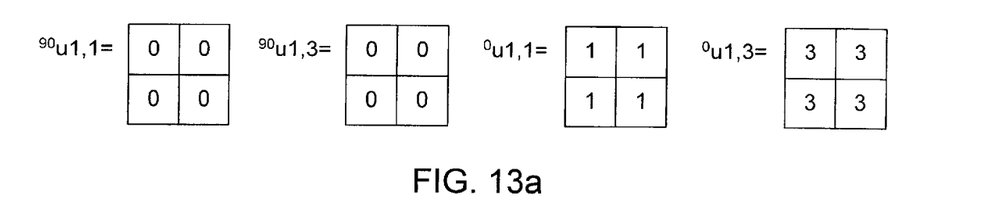
Figure 13B:
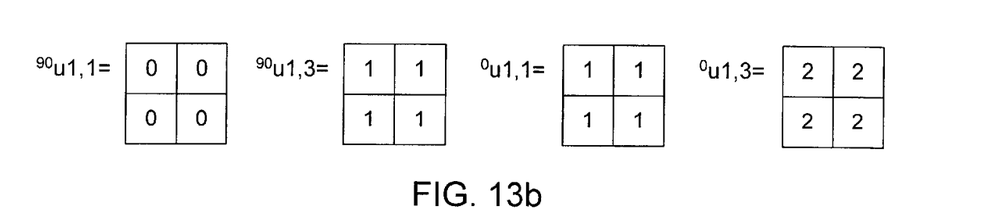
Figure 13C:
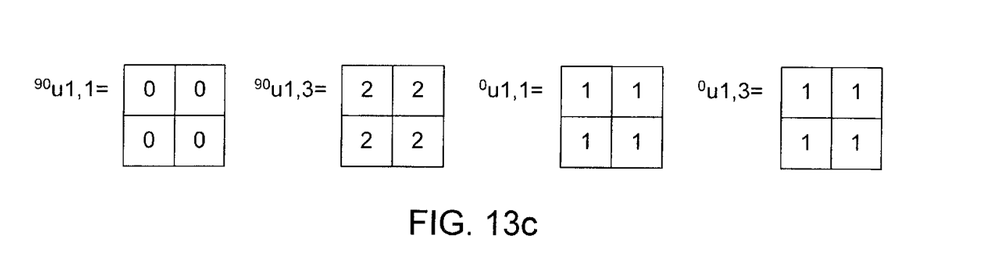

FIG. 12 shows microgradient matrices for the ninety degree offset field $^{90}$m1,1, $^{90}$m1,3 and the zero degree offset field $^0$m1,1, $^0$m1,3. The ninety degree offset field matrices $^{90}$m1,1, $^{90}$m1,3 each have a resolution of 5 mm×1 cm (i.e., the matrices are configured so that the row elements are equal to one another). The zero degree offset field matrices $^0$m1,1, $^0$m1,3 each have a resolution of 1 cm×5 mm (i.e., the matrices are configured so that the column elements are equal to one another). The cell values of the ninety degree offset field matrices $^{90}$m1,1, $^{90}$m1,3 are determined by taking the minimum cell value in each row of the microgradient matrices m1,1 and m1,3, respectively, and setting the other cell in the row equal to the same value. The cell values for the zero degree offset field matrices $^0$m1,1, $^0$m1,3 are determined by finding the smallest value in each column and using the same value for the other cell in the column.

Since the uniform matrices $u_{i,j}$ have gradients equal along both rows and columns, they do not need to be decomposed and can be delivered in combination with the microgradient zero offset field $^0m_{i,j}$. While this is the optimal solution for a single micromatrix v, it is not the most efficient solution when the surrounding micromatrices are taken into account. Thus, it may be more efficient to deliver a portion of the uniform matrix $u_{i,j}$ with the ninety degree offset field $^{90}m_{i,j}$. The amount that is delivered with the zero offset field $^0m_{i,j}$ then becomes a parameter $z_{i,j}$ which is used in an optimization calculation with its values ranging from zero up to the minimum value of the micromatrix $v_{i,j}$ (i.e., cell value of $u_{i,j}$). The parameter $z_{i,j}$ can therefore be defined for each matrix $u_{i,j}$ as follows:

$$^0u_{i,j}(1,1) = {^0u_{i,j}}(1,2) = {^0u_{i,j}}(2,1) = {^0u_{i,j}}(2,2) = z_{i,j};$$

$$z_{i,j} = 0, 1, \ldots, q_{i,j};$$

where: $q_{i,j}$ = minimum cell value of $v_{i,j}$.

There are as many parameters in the optimization problem as there are micromatrices. By varying the optimization parameter $z_{i,j}$ many different decompositions may be formed. An example of the possible zero and ninety degree offset uniform matrices $^0$u1,1, $^0$u1,3, $^{90}$u1,1, $^{90}$u1,3 for the macromatrix V of FIG. 8, are shown in FIGS. 13a–13h.

The parameters $z_{i,j}$ may be chosen by using standard optimization algorithms such as simulated annealing, least squares, or downhill simplex method (described in "Numerical Recipes in C" by Vetterling, Press, Flannery, and Teukolsky, 1992, Cambridge University Press). Other optimization methods may also be used. If a starting point is required for the optimization algorithms, $z_{i,j} = q_{i,j}/2$ may be used.

The optimization involves varying all the $z_{i,j}$ parameters and evaluating the solution in terms of treatment delivery time. Since this is a very involved function that is costly to calculate, a good approximation is to take the maximum sum of the positive gradients along the leaf motion direction for all leaves in both the ninety and zero degree offset fields. For the zero degree offset fields the sum will be taken along the rows of the total zero-offset matrix and for the ninety degree offset fields, the sum will be taken along the columns of the ninety degree offset matrix. Then, the total of the zero degree offset sum and the ninety degree offset sum becomes the function used to choose the best set of parameters. This total sum is preferably minimized.

In order to calculate the positive gradient, a zero is inserted at the beginning of each row and column of the matrix. The gradient is then calculated by adding up positive gradients between adjacent cells. Table 1 shows an example of a positive horizontal gradient calculation for two rows A, B of a matrix. The first row A has a total positive gradient of 2 (0 to 1 for first microcell (+1) and 0 to 1 for third microcell (+1)). Row B has a total positive gradient of 1 (0 to 1 for the first microcell (+1)).

TABLE 1

| A) | 1 | 0 | 1 |
|---|---|---|---|
| B) | 1 | 1 | 1 |

In order to calculate the positive horizontal and vertical gradients for the entire macromatrix V, the respective microgradient matrices $^{0}m1,1$, $^{0}m1,3$, $^{0}m1,1$, $^{90}m1,3$ and uniform matrices $^{0}u1,1$, $^{0}u1,3$, $^{90}u1,1$, $^{90}u1,3$ are added together to form micromatrices $^{0}v1,1$, $^{0}v1,3$, $^{90}v1,1$, $^{90}v1,3$. The zero degree offset micromatrices $^{0}v1,1$, $^{0}v1,3$ are combined (i.e., placed adjacent one another) to form a total zero degree matrix $^{0}T$ and the ninety degree offset micromatrices $^{90}v1,1$, $^{90}v1,3$ are combined to form the total ninety degree matrix $^{90}T$. The total matrix may be defined as:

$$^{0}T = {^{0}U} + {^{0}M}$$

$$^{90}T = {^{90}U} + {^{90}M}$$

Figure 14A:
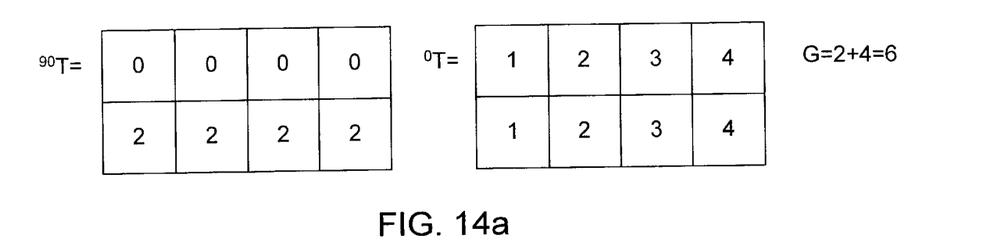
FIGS. 14a–14h illustrate different possible total matrices defined in the optimization process and used to determine an optimum treatment delivery process.
Figure 14B:
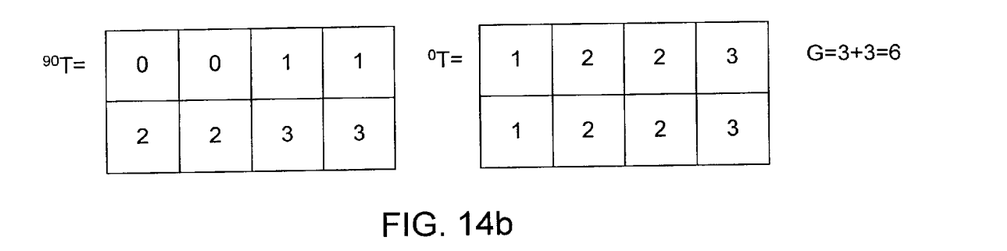
Figure 14C:
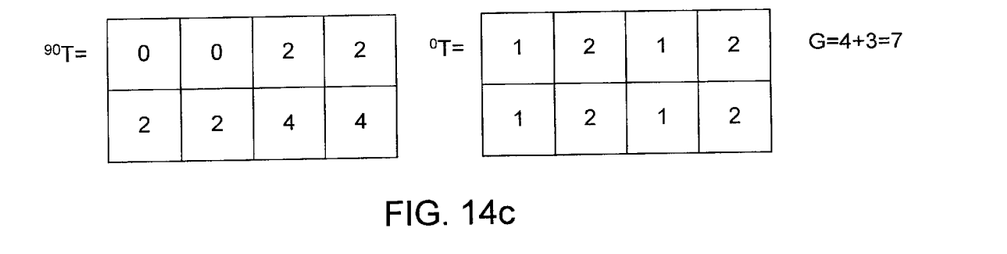
Figure 14D:
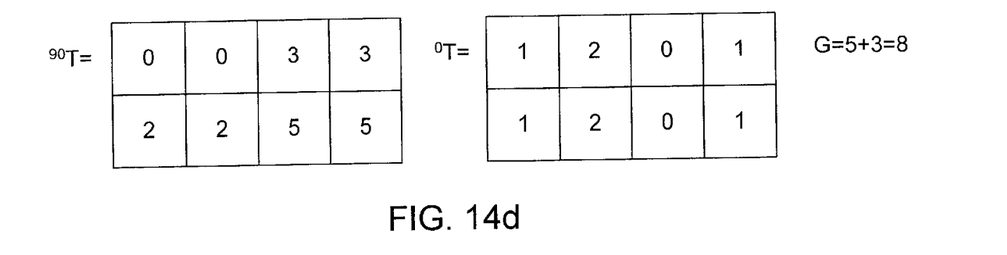
Figure 14E:
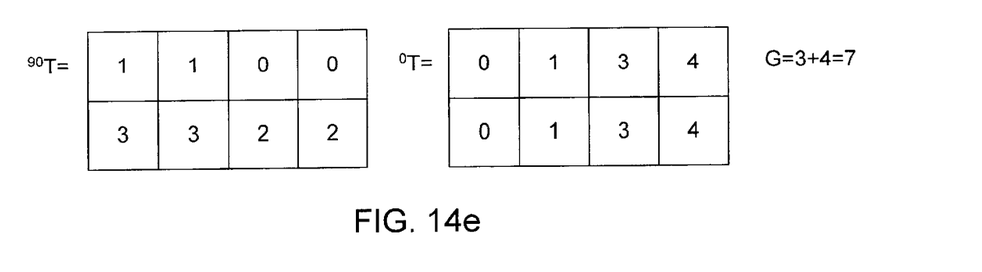
Figure 14F:
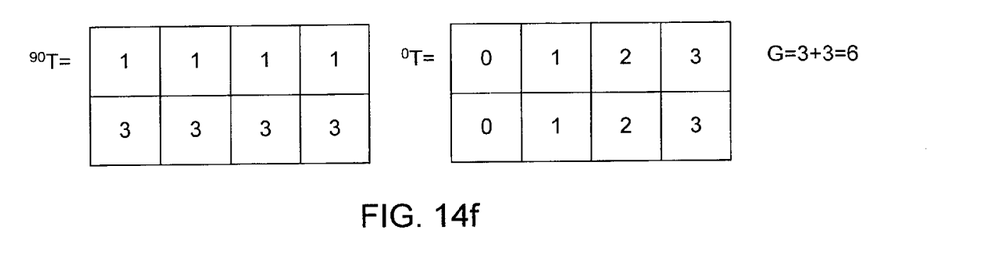
Figure 14G:
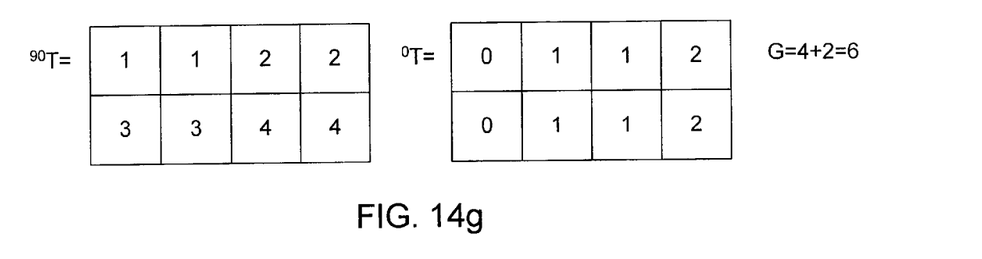
Figure 14H:
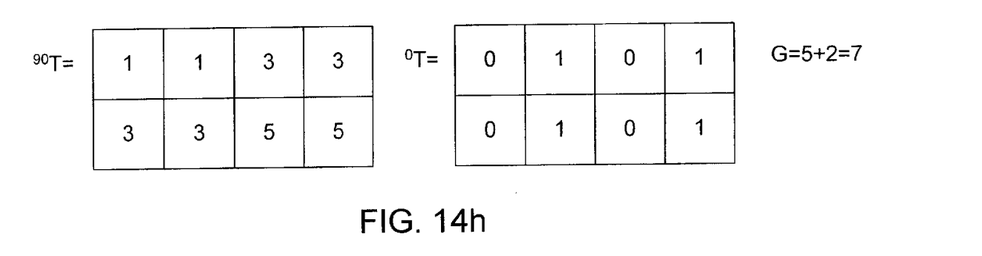

FIGS. 14a–14h show the total zero and ninety degree offset matrices $^{0}T$, $^{90}T$ corresponding to the different possible uniform matrices shown in FIGS. 13a–13h. The total gradient G is calculated by adding the maximum horizontal gradient across all rows of the total zero degree matrix $^{0}T$, and the maximum vertical gradient across all columns of the total ninety degree matrix $^{90}T$. The optimum cases are those with the lowest total gradient (i.e., G=6 in FIGS. 14a, 14b, 14f, and 14g). A number of methods may be used to select the final total matrix from the group of total matrices having the lowest total gradient. One method includes using a series of tie breaking functions to select a final intensity map. For example, one tie breaking function that may be used is the total of all gradients in all leaf directions, not just the maximum. Thus, if the function is identified by R, the matrix shown in FIG. 14a has R=12, the matrix of FIG. 14b has R=11, the matrix of FIG. 14f has R=12, and the matrix of FIG. 14g has R=11. Now only the matrices shown in FIGS. 14b and 14g are tied. These matrices may then be put through another function such as the absolute value of the difference between the maximum horizontal gradient and the maximum vertical gradient. With this function defined as D, the matrix of FIG. 14b has D=3−3=0 and the matrix of FIG. 14g has D=4−2=2. Since the matrix of FIG. 14b has a lower function value D, it is selected as the final matrix.

As previously discussed, another factor to look at when selecting the optimum intensity map is underdosage effects resulting from junctions. Junctions appear between the boundary of a field defined by the tip of a leaf that is common to a boundary of a second non-intersecting field formed by the side of a leaf in a collimator setting orthogonal to that of the first field. Underdosage effects often occur at these junctions between orthogonal fields. The underdosage may occur due to tongue and groove junctions, match line, or rotational junction. The tongue and groove effect results from a junction that is shared between two segments that are used for delivering the intensity map. The match line effect results from two segments sharing a junction within a single leaf pair. The rotational junction occurs when a field border defined by the side of a leaf in one collimator setting is shared by a field border defined by the tip of a leaf in the other collimator setting. The tongue and groove effect may be eliminated by proper sequencing and the match line effect can be corrected by slightly displacing the leaves to move the 50% point of the penumbra to the geometrical field edge. The rotational junction effect cannot be eliminated by proper sequencing, but may be corrected for by a displacement of the leaves.

Figure 15A:
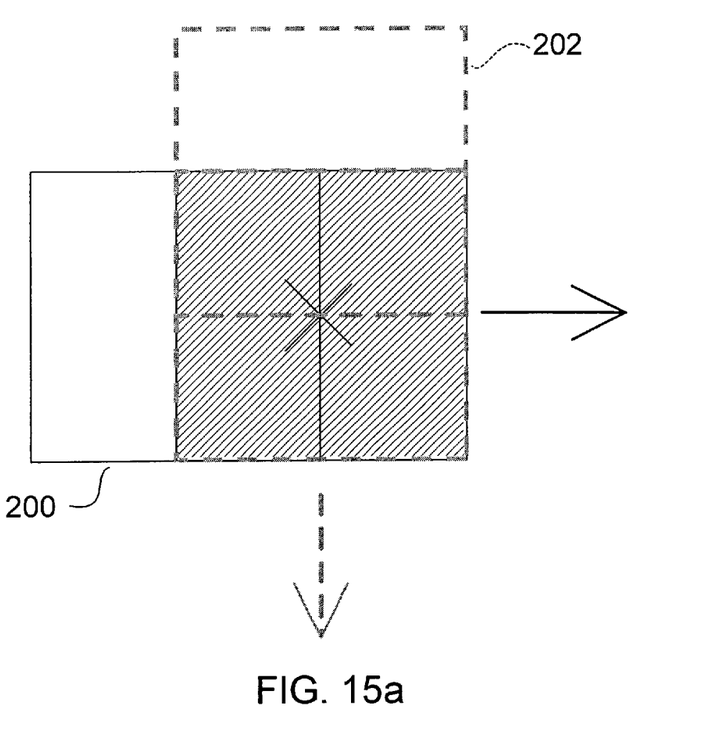
FIG. 15a illustrates unshifted component maps.
Figure 15B:
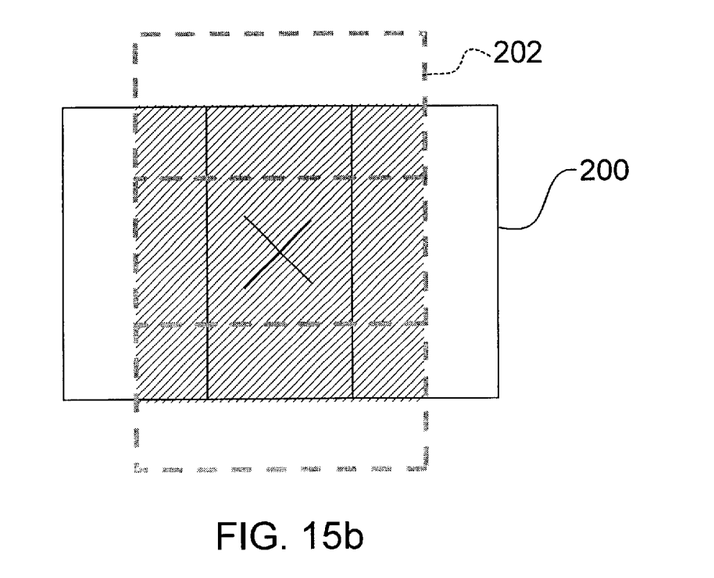
FIG. 15b illustrates the component maps of FIG. 15a shifted 2.5 mm in the zero degree offset and ninety degree offset directions.

Junctions may be avoided by shifting the intensity map grids by half of the original spacing in the leaf motion direction. For example, FIG. 15a illustrates component maps 200, 202 with the isocenter of the maps located on a gridline of the maps. In FIGS. 15a and 15b, the x indicates the location of the isocenter, the solid lines represent the zero-offset component map, the dashed lines form the grid of the ninety degree offset component map, and the hatched squares represent the micromatrix bounded by the leaf edges. The unshifted component maps 200, 202 have gridlines that line up with leaf edges and with the isocenter. In FIG. 15b, the component map is shifted by 2.5 mm (e.g., half of the column and half of the row spacing) in the direction of the arrows of FIG. 15a, so that the isocenter is at the center of a cell rather than on a gridline. This geometry avoids the junction effects, since the gridlines of each component map does not line up with the leaf boundaries in the orthogonal direction.

Another method for minimizing junctions is to split the field into orthogonal components as described above, and shift the leaf position slightly at an unremoved junction to avoid the underdosage effects. For example, the number of junctions that appear between the boundary of a field defined by the tip of a leaf that is common to a boundary of a second non-intersecting field formed by the side of a leaf in a collimator setting orthogonal to that of the first field may also be used as a tie-breaking function in the optimization method described above for minimizing the number of segments. The following describes a method for minimizing junctions while simultaneously minimizing the number of segments.

Figure 16:
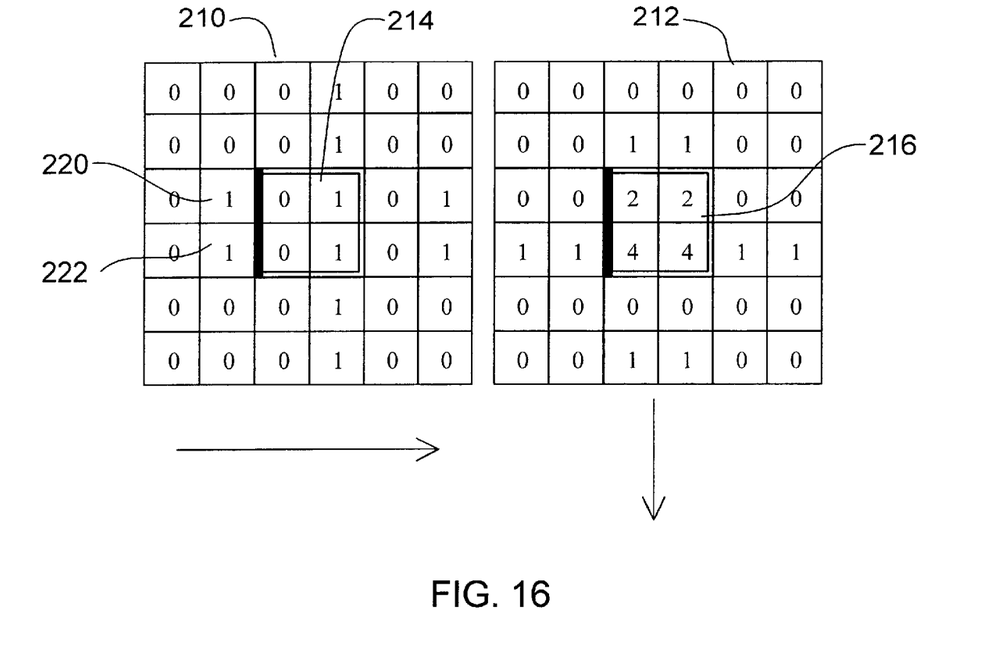
FIG. 16 is an example of a matrix decomposed into component maps having two junctions.

FIG. 16 shows component intensity maps 210, 212 each having a central micromatrix 214, 216, respectively, surrounded by microcells. Both microcells 220, 222 on the left hand side of central micromatrix 214 have junctions (indicated by dark lines). In order to deliver the zero degree intensity map, one of the segments will have its central right leaf tip at the junction (the central left leaf tip is on the left-hand side of the pair of 1s in the second column). In order to deliver the ninety degree offset intensity map, a value of 1 in the first two columns has to be delivered simultaneously with the delivery of a value of 1 in the second two columns, leaving behind a value of 1 and 3 (instead of 2 and 4) in the central micromatrix. To deliver the remainder of this micromatrix, a leaf has to completely block the first and second columns. Thus, at least one segment will have the edge of the leaf in the orthogonal intensity map defining the left border for the fields that deliver the central micromatrix. The location of the left border is the same as the right-hand side border required to deliver the field defined by the pair of 1s in the second column of the zero degree offset map. Since this border is at the same place, it becomes a junction. Since the border applies to both 5 mm×5 mm microcells 220, 222 there are two junctions. These junctions appear where the gradient across them has a different sign in ninety degree offset map 212 as compared to zero degree offset map 210.

Referring again to FIG. 16, the gradient across the junction going from left to right in the zero degree offset map 210 is decreasing (1 to 0), while the corresponding gradient across the same junction in the ninety degree offset map 212 is increasing (0 to 2). The locations of the junctions are found where the following conditions are violated:

if $\Delta T_0(i,j) \geq 0$ then $0 \leq \Delta^0 T(i,j) \leq \Delta T_0(i,j)$ if $\Delta T_0(i,j) < 0$ then $0 \geq \Delta^0 T(i,j) \geq \Delta T_0(i,j)$ if $\Delta T_{90}(i,j) \geq 0$ then $0 \leq \Delta^{90} T(i,j) \leq \Delta T_{90}(i,j)$ if $\Delta T_{90}(i,j) < 0$ then $0 \leq \Delta^{90} T(i,j) \geq \Delta T_{90}(i,j)$ where:

$$\Delta T_0(i,j) = T(i,j) - T(i, j-1) \quad j > 0$$
$$= T(i,j), \quad j = 0$$
$$\Delta T_{90}(i,j) = T(i,j) - T(i-1, j) \quad i > 0$$
$$= T(i,j) \quad i = 0$$
$$i, j = 0, 2, 4 \ldots$$

If $J(P(k,l))$ is defined as the number of junctions that exist with a given $P(k,l)$, $P_i$ is the current parameter value, $P_f$ is the parameter value after the parameter has been changed, and $\Delta J$ is the number of changes in junctions, then the following quantity needs to be minimized to reduce the number of junctions:

$$\Delta J = J(P_f) - J(P_i)$$

Due to the large number of possibilities typically available for an intensity map, an optimization method is preferably used to minimize the number of junctions and segments required to deliver the intensity map The following describes one example for selecting a final configuration.

Figure 17:
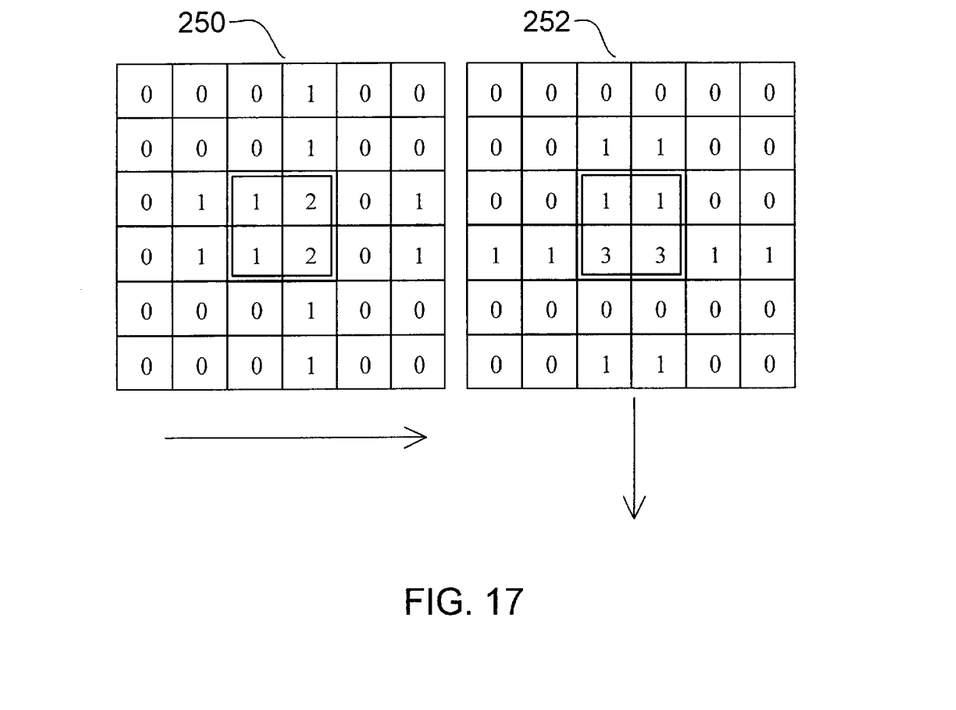
FIG. 17 illustrates the component maps of FIG. 16 modified to remove the junctions.

An initial configuration may be selected, for example, where the uniform component for the zero degree offset map and ninety degree offset map are the same. Then, the positive gradient sum in each row in $^0T$ and each column in $^{90}T$ is examined, and the array (i.e., the row or column) that has the maximum is found. If there is a tie, then the tie is broken by choosing the array that has the least number of peaks (since these arrays have the most potential for change). If there is still a tie, the array with the greatest number of junction conditions is chosen. Within the array, the micromatrix which has the greatest effect on the number of junctions (i.e., minimizes equation $\Delta J = J(P_f) - J(P_i)$) is identified. If there is a tie, the gradients across the borders of the micromatrix is looked at, since the gradient inside a micromatrix is not affected by the variation of the uniform component. If the absolute value of the difference between these gradients is large, and the gradients have opposite signs, then by changing the uniform value to reduce the difference between these gradients, the peaks and valleys are flattened out. This can be expressed as follows:

$|\Delta^0 T_p(i,j)|$ $|\Delta^{90} T_p(i,j)|$ $\Delta^0 T_p(i,j) = \Delta^0 T(i,j) - \Delta^0 T(i,j+2)$ $\Delta^{90} T_p(i,j) = \Delta^{90} T(i,j) - \Delta^{90} T(i+2)$ Referring again to FIG. 16, the gradient going down into the central micromatrix in the middle column of $^{90}T$ is $(2-1)=1$, while the gradient leaving the central micromatrix is $(0-4)=-4$, resulting in a difference of 5, according to the above equations. Since this number is positive, it indicates the presence of a peak and the uniform value needs to be lowered to reduce this peak. The uniform value at this stage is 2. By reducing it to 1, the component intensity maps are modified and result in maps 250, 252, as shown in FIG. 17. The junctions are eliminated and a lower beam time is obtained.

After finding the micromatrix within the chosen array, the uniform value for that micromatrix can be changed by a fraction (e.g., ½ or less) of the gradient difference across the micromatrix. The new configuration is evaluated by counting the number of junctions and by segmenting both the zero degree offset and ninety degree offset maps to determine delivery time, since the maximum positive gradient sum does not consider segmentation constraints such as the elimination of the tongue and groove effect. If the configuration yields better results, it is kept; otherwise it is ignored and the parameter change (i.e., the adjustment of the uniform value) is removed. The optimization proceeds through several iterations by choosing which micromatrix to change, while excluding the micromatrices that have already been chosen. When the limit of no improving iterations is reached, the optimization process is completed.

Although the present invention has been described in accordance with the embodiments shown, one of ordinary skill in the art will readily recognize that there could be variations to the embodiment and these variations would be within the spirit and scope of the present invention. Accordingly, many modifications may be made by one of ordinary skill in the art without departing from the spirit and scope of the appended claims.

What is claimed is:

1. A method for controlling radiation delivery from a radiation source to an object, comprising:

defining a field on the object for radiation delivery, said field including a plurality of cells each having a defined treatment intensity level;

grouping the cells to form a plurality of matrices, each of the matrices having at least one dimension approximately equal to a width of a collimator leaf capable of blocking radiation emitted from the radiation source;

decomposing each of the matrices into orthogonal matrices; and optimizing delivery of the radiation by combining orthogonal matrices from each of the matrices and selecting a combination of orthogonal matrices to minimize junction effects.

2. The method of claim 1 wherein minimizing junction effects comprises minimizing rotational junction effects.

3. The method of claim 1 wherein minimizing junction effects comprises shifting orthogonal matrices to relocate an isocenter relative to the matrices.

4. The method of claim 1 wherein minimizing junction effects comprises modifying a matrix having the greatest effect on the number of junctions.

5. The method of claim 4 further comprising evaluating gradients across adjacent matrices.

6. The method of claim 1 wherein optimizing delivery comprises selecting a combination of orthogonal matrices having minimum vertical and horizontal gradients and wherein minimizing junction effects comprises modifying the selected combination of orthogonal matrices.

7. The method of claim 1 wherein decomposing the matrix into orthogonal matrices comprises decomposing the matrix into a uniform matrix composed of cells each having an intensity level equal to the minimum cell intensity level of the matrix and a microgradient matrix having cells equal to the intensity level of the cells of the matrix minus the respective cells of the uniform matrix.

8. The method of claim 7 further comprising decomposing the uniform matrix to form a plurality of uniform orthogonal matrices.

9. The method of claim 8 further comprising decomposing the microgradient matrix to form two microgradient orthogonal matrices.

10. The method of claim 9 wherein optimizing delivery of the radiation further comprises adding the uniform and microgradient orthogonal matrices to form said orthogonal matrices and combining said orthogonal matrices of each of the respective matrices to form total orthogonal matrices.

11. The method of claim 1 further comprising defining an opening between the radiation source and said field on the object, said opening being defined by at least two collimator leaves positioned based on the selected orthogonal matrices.

12. The method of claim 11 wherein the cells each have a width and height of approximately one half the width of the collimator leaves.

13. The method of claim 12 wherein each of the collimator leaves has a width of approximately one centimeter.

14. The method of claim 13 wherein the cells each have a width and height of approximately 5 millimeters.

15. The method of claim 11 wherein the opening allows for delivery of said radiation with a resolution of approximately one half the width of the leaves.

16. The method of claim 1 wherein grouping the cells comprises grouping four square cells to form the matrix.

17. The method of claim 1 wherein the orthogonal matrices each have a resolution in a first direction approximately equal to the leaf width and a resolution in a second direction higher than the resolution in said first direction.

18. The method of claim 17 wherein said second direction is generally orthogonal to said first direction.

19. The method of claim 1 wherein optimizing delivery of the radiation further comprises evaluating vertical and horizontal gradients of the orthogonal matrices.

20. A system for controlling radiation output to an object from a radiation source, said object having a field defined thereon for radiation delivery, said field including a plurality of cells having predefined treatment intensity levels, the system comprising:
 a collimator having multiple leaves for blocking radiation from said source and defining an opening between the radiation source and said object; and
 a processor for receiving the cells, grouping a portion of the cells to form a matrix having at least one dimension approximately equal to a width of one of the collimator leaves, decomposing the matrix into orthogonal matrices, and optimizing delivery of the radiation by combining orthogonal matrices from each of the matrices and selecting a combination of orthogonal matrices to minimize junction effects.

21. The system of claim 20 wherein the leaves of the multi-leaf collimator each have a width of approximately one centimeter.

22. The system of claim 20 wherein the cells have a width and height of approximately one half the width of the collimator leaves.

23. The system of claim 20 wherein the leaves are movable in a first direction generally perpendicular to a delivery direction of the radiation to form said opening between the radiation source and said object, said opening being defined by at least two of the collimator leaves positioned based on the selected orthogonal matrices.

24. The system of claim 23 wherein the leaves are movable in a second direction generally perpendicular to said delivery direction and said first direction.

25. The system of claim 23 wherein the multi-leaf collimator is operable to provide radiation treatment with a resolution approximately one half of the width of the leaves.

26. The system of claim 20 wherein vertical gradients of the matrix are equal to one another and horizontal gradients of the matrix are equal to one another.

27. The system of claim 20 wherein the processor is operable to select a combination of orthogonal matrices having minimum vertical and horizontal gradients and modify the selected combination of orthogonal matrices to minimize junction effects.

28. A method for controlling radiation delivery from a radiation source to an object, comprising:
 defining a field on the object for radiation delivery, said field including a plurality of cells each having a defined treatment intensity level;
 grouping the cells to form a plurality of matrices, each of the matrices having at least one dimension approximately equal to a width of a collimator leaf capable of blocking radiation emitted from the radiation source;
 decomposing each of the matrices into orthogonal matrices; and
 optimizing delivery of the radiation by shifting orthogonal matrices to relocate an isocenter relative to the matrices.

29. A method for defining an intensity map for use in delivering radiation from a radiation source to an object, the method comprising:
 defining a field on the object for radiation delivery, said field including a plurality of cells each having a defined treatment intensity level;
 grouping the cells to form a plurality of matrices;
 decomposing each of said matrices into orthogonal matrices; and
 creating an intensity map by selecting a combination of orthogonal matrices to minimize junction effects.

* * * * *